US006855554B2

(12) United States Patent
Fritsche et al.

(10) Patent No.: US 6,855,554 B2
(45) Date of Patent: Feb. 15, 2005

(54) METHODS AND COMPOSITIONS FOR DETECTION OF BREAST CANCER

(75) Inventors: Herbert A. Fritsche, Houston, TX (US); Henry M. Kuerer, Houston, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

(21) Appl. No.: 10/236,027

(22) Filed: Sep. 5, 2002

(65) Prior Publication Data

US 2003/0077832 A1 Apr. 24, 2003

Related U.S. Application Data

(60) Provisional application No. 60/324,148, filed on Sep. 21, 2001.

(51) Int. Cl.[7] ............................................. G01N 33/48
(52) U.S. Cl. .............................. 436/64; 436/63; 436/86; 436/177; 436/178; 204/450; 204/456; 204/461
(58) Field of Search ........................... 436/63, 64, 86, 436/164, 174, 177, 178; 204/450, 456, 461

(56) References Cited

U.S. PATENT DOCUMENTS

| | | | | |
|---|---|---|---|---|
| 5,914,238 A | * | 6/1999 | Keesee et al. ............. | 435/7.23 |
| 6,064,754 A | | 5/2000 | Parekh et al. ............... | 382/129 |
| 6,128,608 A | | 10/2000 | Barnhill ...................... | 706/16 |
| 6,157,921 A | | 12/2000 | Barnhill ...................... | 706/16 |
| 6,287,521 B1 | * | 9/2001 | Quay et al. ................. | 422/101 |
| 6,427,141 B1 | | 7/2002 | Barnhill ...................... | 706/16 |
| 6,471,660 B1 | * | 10/2002 | Covington .................. | 600/584 |
| 2001/0034038 A1 | * | 10/2001 | Hung ......................... | 435/7.23 |
| 2002/0111742 A1 | | 8/2002 | Rocke et al. ................ | 702/19 |
| 2003/0087265 A1 | * | 5/2003 | Sauter et al. ................ | 435/6 |
| 2003/0152935 A1 | * | 8/2003 | Chandrasiri Herath ......... | 435/6 |

FOREIGN PATENT DOCUMENTS

| WO | WO 0223200 | | 3/2002 |
|---|---|---|---|
| WO | 03/044485 | * | 5/2003 |

OTHER PUBLICATIONS

Paweletz et al. Disease Markers, vol. 17, 2001, pp. 301–307.*
Klein et al. The Breast Journal, vol. 7, No. 6, 2001, pp. 378–387.*
Boser et al., In: *Proceedings of the 5th Annual ACM Workshop on Computational Learning Theory*, ACM Press, Pittsburgh, PA, 144–152, 1992.
Brown et al., "Knowledge–based analysis of microarray gene expression data by using support vector machines," *Proc. Natl. Acad.Sci. USA*, 97:262–267, 2000.
Cristianini et al., In: *An Introduction to Support Vector Machines*, Cambridge Univ. Press, Cambridge, www.support–vector.net, 2000.
Furey et al., "Support vector machine classification and validation of cancer tissue samples using microarray expression data," *Bioinformatics*, 16:906–914, 2000.
Golub et al., "Molecular classification of cancer: class discovery and class prediction by gene expression monitoring," *Science*, 286:531–537, 1999.

(List continued on next page.)

*Primary Examiner*—Maureen M. Wallenhorst
(74) *Attorney, Agent, or Firm*—Fulbright & Jaworski

(57) ABSTRACT

Systematic comparisons of breast ductal fluid samples obtained by nipple aspiration from women with unilateral breast cancer revealed significant differences in ductal fluid protein expression between the breast with cancer and the breast without cancer in each patient. This study demonstrates that breast ductal fluid contains over 1000 separate protein species and suggests that ductal fluids from breast cancer patients may be useful for high-throughput biomarker discovery.

29 Claims, 10 Drawing Sheets

OTHER PUBLICATIONS

Jaakkola et al., "Using the fisher kernal method to detect remote protein homologies," In: *Proceedings of the 7th International Conf. On Intelligent Systems for Molecular Biology*, AAAI Press, Menlo Park, CA, 1999.

Kuerer, M., Presentation given by Henry Kuerer at M.D. Anderson Cancer Cener, Houston, TX in Mar. 2002 and May 2001.

Mukhejee et al., "Support vector machine classification of microarray data," In: *Technical Report CBCL*, Paper 182/AI Memo 1676, MIT, 1999.

Newton, "Analysis of microarray gene expression data using machine learning techniques," *CMPUT Computational Molecular Biology & Bioinformatics*, Presentation 2002.

Okazaki et al., "Fiberoptic Ductoscopy of the breast: a new diagnostic procedure for nipple discharge," *Jpn. J. Clin. Oncol.*, 21:188–193, 1991.

Petrakis, "Nipple aspirate fluid in epidemiologic studies of breast disease," *Epidem. Rev.*, 15:188–195, 1993b.

Petrakis, "Physiologic, biochemical, and cytologic aspects of nipple aspirate fluid," *Breast Cancer Res Treat.*, 8:7–19, 1986.

Petrakis, "Studies on the epidemiology and natural history of benign breast disease and breast cancer using nipple aspirate fluid," *Cancer Epidem. Biomarker Prev.*, 2:3–10, 1993.

Petricoin et al., "Use of proteomic patterns in serum to identify ovarian cancer," *Lancet*, 359, 572–577, 2002.

Sartorius et al., "Contrast ductography for recognition and localization of benign and malignant breast lesions: an improved technique," In: *Breast Carcinoma*, Logan (Ed), Wiley, NY, NY, 281–300, 1977.

Sartorius, "The biochemistry of breast cyst fluids and duct secretions," *Breast Cancer Res. Treat.*, 35:255–266, 1995.

Vita et al., "Novel miniproteins engineered by the tarnsfer of active sites to small natural scaffolds," *Biopolymers*, 47:93–100, 1998.

Wrensch et al., "Breast cancer incidence in women with abnormal cytology in nipple aspirates of breast fluid," *Am. J. Epidem.*, 135:130–141, 1992.

Wrensch et al., "Breast fluid cholesterol and cholesterol $\beta$–epoxide concentrations in women with benign breast disease," *Cancer Res.*, 49:2168–2174, 1989.

Wrensch et al., "Factors associated with obtaining nipple aspirate fluid: analysis of 1428 women an dliterature review," *Breast Cancer Res. Treat.*, 15:39–51, 1990.

Zien et al., "Engineering support vector machine kernels that recognize translation initiation sites," *Bioinformatics*, 16:799–807, 2000.

* cited by examiner

METHODS AND COMPOSITIONS FOR DETECTION OF BREAST CANCER

The present application claims priority to co-pending U.S. Patent Application Serial No. 60/324,148 filed Sep. 21, 2001. The entire text of the above-referenced disclosure is specifically incorporated by reference herein without disclaimer.

BACKGROUND OF THE INVENTION

1. Field of the Invention

The present invention relates generally to the fields of cancer biology and molecular biology. More particularly, it concerns the method of detecting cancer and identifying cancer biomarkers from nipple aspiration fluid.

2. Description of Related Art

Breast cancer is the most common fatal malignancy in women. About 15% of all women will be diagnosed with breast cancer during their lifetime. In the United States, breast cancer is the third leading cause of death in women. Despite recent progress in early detection, as well as improved treatment, the mortality rate remains unchanged. Early diagnosis is the key to surviving breast cancer. Typically, the detection of breast cancer involves an exam by a physician, a mammogram, and either a needle aspiration or biopsy. When the breast tissue forming the lump is removed, the tissue is examined for possible cancer cells.

Analysis of the biochemical and cellular contents of breast ductal fluid has recently gained attention as a potential non-invasive method for studying the local microenvironment associated with the development and progression of breast cancer. Breast cancer arise from the ductal or lobular units of the breast. These units secrete into an average of six to nine ducts, and the secretions are easily accessible as they exit each breast through separate orifices at the nipple. Because of the increased interest in analysis of breast ductal fluid, interest in nipple aspiration of breast ductal fluid—a method first used in the 1970s—has recently become renewed. In nipple aspiration, a simple, handheld suction cup is placed on the nipple and used to quickly and non-invasively obtain a concentrated fluid fraction of breast secretions. This technique is successful in most women. Much of the earlier groundbreaking work with breast ductal fluid obtained by nipple aspiration (nipple aspiration fluid, or NAF) was performed either in healthy volunteers or in women with benign breast disease. However, analysis of NAF has not been done to generate information regarding breast tissue that is cancerous or that has a tumor.

There is a continued need for diagnostic and therapeutic approaches related to breast cancer.

SUMMARY OF THE INVENTION

It is believed that a new application of nipple aspiration—obtaining ductal fluid samples from a breast containing a known carcinoma and the same patient's healthy contralateral breast (as an internal control) and comparing the protein expression profiles of these samples—may be a practical method for identifying clinically relevant tumor markers that may be useful in risk stratification, diagnosis, treatment monitoring, and detection of cancer recurrence.

The present invention is based on the discovery and development of a system for identifying protein markers or a pattern of protein markers that indicate breast cancer in a patient. One or more of the identified markers or the pattern of markers can then be used in diagnosis, prognosis, and/or treatment regimens related to breast cancer.

The invention involves generating a pattern of proteins in a sample using two-dimensional gel electrophoresis to identify differences between cancerous and noncancerous samples from the same patient. The method can be used to identify both unilateral (cancer in a single breast) and bilateral (cancer in both breasts) types of breast cancer. Methods of the invention are specifically contemplated to detect breast cancer in female patients.

In some embodiments of the invention, there are methods for identifying a marker for breast cancer comprising: a) collecting a first sample having nipple aspiration fluid from a cancerous breast of a cancer patient; b) collecting a second sample having nipple aspiration from a noncancerous breast of the cancer patient, wherein the first and second samples comprising fluid from cancerous and noncancerous breasts of the same cancer patient constitutes a paired sample; c) separating breast fluid proteins within each of the samples by two-dimensional gel electrophoresis; and, d) comparing the profiles of breast fluid proteins from the first and second samples, wherein a difference in the profiles identifies a breast cancer marker. Two-dimensional (2-d) gel electrophoresis of a sample will generate a protein profile for that sample based on the size and charge of the proteins in the sample. The profile can then be used to identify the presence or absence of a particular protein in sample, as well as identify whether the amount of that protein is changed. In addition a protein's position or location in a profile may also be altered by other chemical alteration of the protein, such as postranslational processing. The present invention concerns identifying one or more markers of breast cancer based on differences in protein profiles of a paired sample (from the same patient), and based on accumulated data generated from the differences in profiles of multiple paired samples.

In some embodiments of the invention, a difference in a paired sample is detected. Multiple paired samples from different patients are used, in some methods of the invention, to generate a protein pattern based on multiple protein profiles from different patients. A protein pattern is generated by comparing each profile from each patient sample and identifying those spots or proteins that are similarly modulated between the different patient samples or paired samples, thereby accumulating a pattern indicative of breast cancer that may be used to diagnose development or progression of the disease in any patient sample. Furthermore, the generation of such a pattern would be used as a standard in diagnosing breast cancer in any patient having breast cancer.

In still further embodiments, the present invention comprising generating a computer-assisted image of the profiles generated by two-dimensional gel electrophoresis prior to comparing the profiles. These digitalized images may be produced by any method, which are well known to those of skill in the art. The images may be analyzed by direct visualization by a person or by inputting the data into a machine that can evaluate it, such as a learning algorithm.

In further embodiments a learning algorithm is employed to compare the computer-assisted images of the profiles. In still further embodiments, the learning algorithm is a trained support vector machine. Learning algorithms may be employed not only to compare individual paired samples, but also to compare and analyze multiple paired samples in order to detect a pattern of proteins that identifies a breast cancer patient. Thus, in additional methods of the invention, multiple paired samples from cancer patients are collected, compared (one sample compared to the other sample in the paired sample), and then analyzed. The method involves analyzing the profiles of the paired samples to identify a pattern of breast proteins in which a breast cancer marker is identified.

In further embodiments, the present invention comprises staining of the breast fluid proteins as part of the 2-D gel electrophoresis process using a variety of protein staining techniques. Methods of the invention involve, in some embodiments, exposing the 2-D electrophoresed gel to silver staining, fluorescent staining, or a colorimetric or enzymatic dye. In further embodiments, the dye is ponceau S, streptavidin-alkaline phosphatase, coomassie blue or ruby red.

A noncancerous sample may be from any tissue, culture, cell, or specimen that is noncancerous. In some embodiments of the invention, a noncancerous sample is nipple aspiration fluid from a breast that is not cancerous or that does not have a tumor, while in other embodiments the noncancerous sample is a blood sample. A cancerous sample will be tissue, cells, fluid, or other collection from a breast that is cancerous (may initially be only suspected of being cancerous). In certain embodiments of the invention, the sample contains nipple aspiration fluid. Nipple aspiration fluid may be collected from a patient using a mild suction device.

It is contemplated that multiple cancer markers among the breast cancer proteins may be identified. At least 1, 2, 3, 4, 5, 6, 7, 8, 9, 10 or more breast cancer markers are identified by methods of the invention. These markers may then be the direct basis for diagnosing, prognosing, or treating a patient with breast cancer. A sample from a patient suspected of having cancer will be assayed for one or more of the breast cancer markers using methods well known to those of skill in the art, including immunochemical assays or nucleic acid-based assays. In certain embodiments of the invention, kits for identifying breast cancer markers identified by methods of the invention are specifically contemplated as part of the invention.

In some embodiments of the invention, there is a method of detecting development or progression of breast cancer in a patient comprising: a) collecting a sample comprising nipple aspiration fluid from at least one breast of the patient; b) separating breast fluid proteins in the sample by two-dimensional gel electrophoresis; and, c) analyzing the profile of breast fluid proteins from the sample to detect a breast cancer marker identified by screening methods described above.

Furthermore, there are methods of detecting development or progression of breast cancer in a patient involving: a) collecting a sample comprising nipple aspiration fluid from at least one breast of the patient; and b) assaying the sample for a breast cancer marker identified by screening methods described above. In some embodiments, there is a method of detecting development or progression of breast cancer in a patient comprising: a) collecting a first sample comprising nipple aspiration fluid from a cancerous breast of a cancer patient; b) collecting a second sample comprising nipple aspiration from a noncancerous breast of the cancer patient, wherein the first and second samples comprising fluid from the cancerous and noncancerous breasts of the same cancer patient constitutes a paired sample; c) separating breast fluid proteins within each of the samples by two-dimensional gel electrophoresis; and, d) comparing the profiles of breast fluid proteins from the first and second samples, wherein a difference in the profiles identifies a breast cancer marker.

Other embodiments of the invention include a method for detecting development or progression of breast cancer in a patient comprising: a) collecting a blood serum sample from the breast cancer patient; b) collecting a nipple aspiration fluid sample from a cancerous breast of the breast cancer patient; c) separating blood serum proteins and breast fluid proteins by two-dimensional polyacrylamide gel electrophoresis; and, d) comparing the profile of blood serum proteins with the profile of breast fluid proteins, wherein a difference in the profiles identifies a breast cancer marker.

These various methods may employ any of the embodiments described herein. It is specifically contemplated that one embodiments discussed with one aspect of the invention may be applied to any other aspect of the invention, and vice versa.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
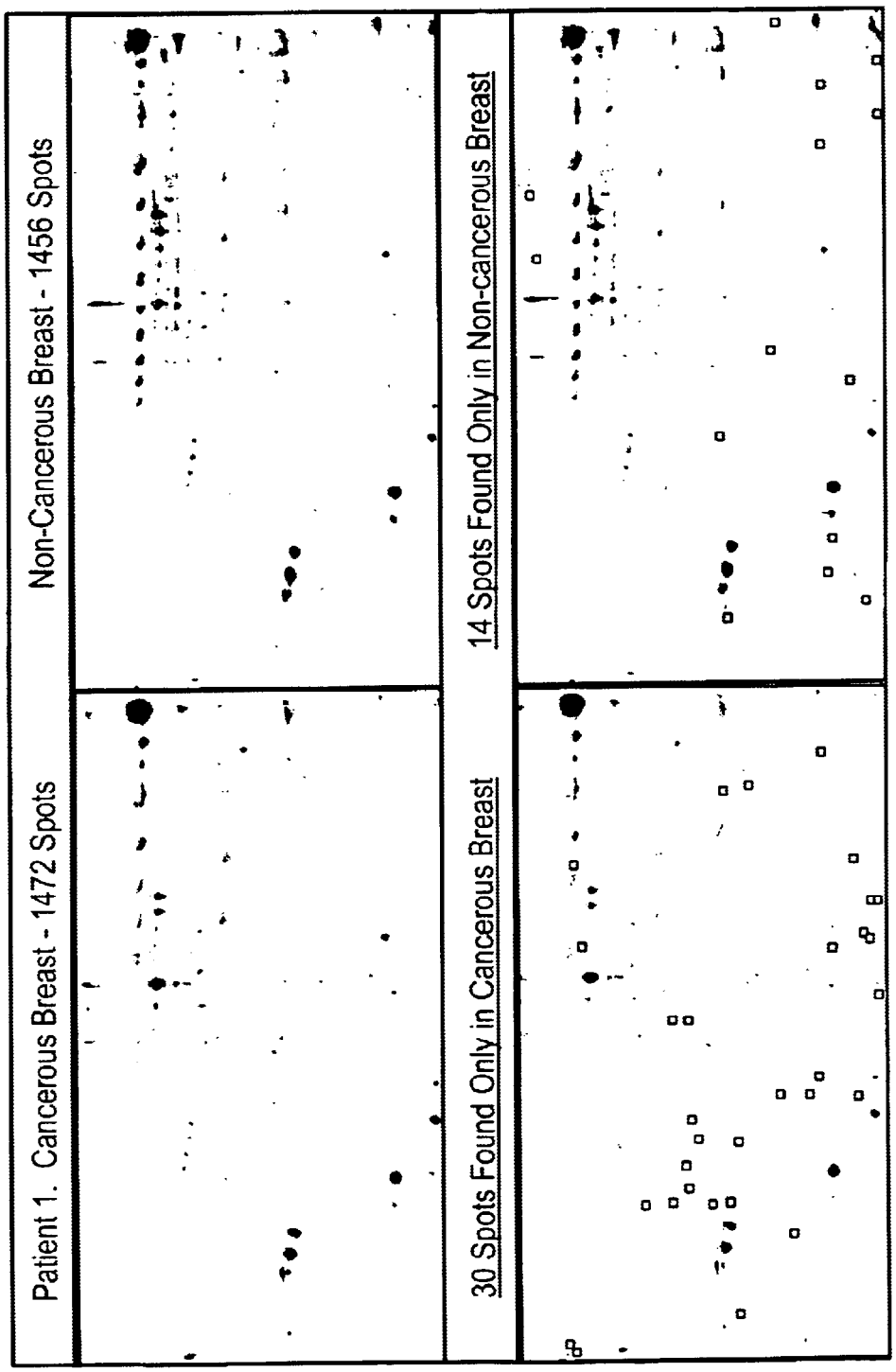
FIGS. 1A–1D. Profiles of protein expression on two-dimensional polyacrylamide gel electrophoresis from nipple aspiration fluid samples from three women diagnosed with unilateral invasive breast cancer (FIGS. 1A–1C) and one healthy subject 4 without evidence of cancer in either breast (FIG. 1D). In each set, the upper panels show all the protein spots detected the indicated breast, and the lower panels show all the proteins found in this breast but not the patient's contralateral breast. The numbers by the unique spots in the lower panels are position designations provided by computerized analysis of the data points.

Since breast cancer usually arises from a single ductal system and exists in a precancerous state for a number of years, fluid collection from individual breast ducts from the same patient holds great diagnostic promise for the identification of cancer markers.

1. The Present Invention

Early detection of breast cancer can be accomplished by analysis of nipple aspirate fluid using a non-invasive method for studying the local microenvironment associated with the development and progression of breast carcinoma. Thus, in particular embodiments the present invention uses nipple aspiration fluid to detect the development and progression of breast cancer in a patient having breast cancer comprising collecting the nipple aspirate fluid; separating the protein in the nipple aspirate fluid by two-dimensional gel electrophoresis; providing the protein data to a support vector machine; and analyzing the protein expression profiles. By comparing the protein profiles of the cancerous breast to the non-cancerous breast from the same patient the present invention seeks to identify biomarkers for breast cancer.

The assay of the nipple aspiration fluid can be accomplished by two-dimensional (2D) gel electrophoresis using commercially available reagents. Stained spots represent proteins or lipids. Staining of the proteins obtained by 2D gel electrophoresis can be accomplished with calorimetric dyes (coomassie), silver staining and fluorescent staining (Ruby Red). Similar staining for lipids can also be performed. In the present invention, a 2D-gel profile obtained from the cancer breast is compared with the normal breast from the same patient, and protein losses and gains are observed. Analysis of the digitized 2D-gel profiles by the SVM (support vector machine) pattern recognition methods and system can identified characteristic cancer patterns or individual protein markers that are diagnostic of breast cancer.

Most breast cancers originate in the milk ducts, and thus, it seems likely that protein and lipid products of tumors will be secreted into the ductal fluid. In one embodiment of the present invention, this fluid can be aspirated with a mild suction device applied to the nipple after warming and with gentle massage of the breast. The nipple aspiration fluid (NAF) is placed into a premeasured volume of a buffer containing a variety of proteolytic inhibitors and stored frozen at −80° C. until assayed.

Nipple aspiration and/or the introduction of contrast medium into breast ducts prior to imaging are described in Sartorius (1995); Satorious et al. (1977); Petrakis (1993a); Petrakis (1993b); Petrakis (1986); Wrensch et al. (1992); Wrensch et al. (1990); Wrensch et al. (1989). The use of a 0.4 mm flexible scope to investigate nipple discharge is described in Okazaki et al. (1991).

II. Proteinaceous Compositions of Nipple Aspiration Fluid

In particular embodiments, that present invention employs a method of identifying protein markers for breast cancer by comparing the profiles of breast proteins collected from nipple aspiration fluid, and separated by 2D gel electrophoresis, from a cancer and non-cancerous breast of the same patient. Such cancer proteins may be used as diagnostic tools in breast cancer. Thus, in certain embodiments, the present invention concerns novel compositions comprising at least one proteinaceous molecule. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

Once a cancer marker is identified, assays may be employed to determine whether that marker is present in a particular sample for diagnostic, prognostic, or therapeutic purposes in a cancer patient or a patient suspected of having cancer. Assays to identify a particular protein are well-known to those of ordinary skill in the art. Such assays may involve identifying a nucleic acid encoding the marker or using an antibody that specifically recognizes the marker. Thus, the present invention concerns proteinaceous compositions that are antibodies for use in protein assays to detect the presence of a breast cancer marker.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide.

In certain embodiments, the proteinaceous composition may comprise at least one antibody. It is contemplated that antibodies to specific tissues may bind the tissue(s) and foster tighter adhesion of the glue to the tissues after welding. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

It is contemplated that virtually any protein, polypeptide or peptide containing component may be used in the compositions and methods disclosed herein. However, it is preferred that the proteinaceous material is biocompatible. In certain embodiments, it is envisioned that the formation of a more viscous composition will be advantageous in that it will allow the composition to be more precisely or easily applied to the tissue and to be maintained in contact with the tissue throughout the procedure. In such cases, the use of a peptide composition, or more preferably, a polypeptide or protein composition, is contemplated. Ranges of viscosity include, but are not limited to, about 40 to about 100 poise. In certain aspects, a viscosity of about 80 to about 100 poise is preferred.

Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide which is derived or obtained from an organism. Organisms that may be used include, but are not limited to, a bovine, a reptilian, an amphibian, a piscine, a rodent, an avian, a canine, a feline, a fungal, a plant, or a prokaryotic organism, with a selected animal or human subject being preferred. The "autologous protein, polypeptide or peptide" may then be used as a component of a composition intended for application to the selected animal or human subject. In certain aspects, the autologous proteins or peptides are prepared, for example from whole plasma of the selected donor. The plasma is placed in tubes and placed in a freezer at about −80° C. for at least about 12 hours and then centrifuged at about 12,000 times g for about 15 minutes to obtain the precipitate. The precipitate, such as fibrinogen may be stored for up to about one year (Oz, 1990).

To select other proteins, polypeptides, peptides and the like for use in the methods and compositions of the present invention, one would preferably select a proteinacous material that possesses one or more of the following characteristics: it forms a solution with a high percentage of proteinaceous material solubilized; it possesses a high viscosity (i.e. about 40 to about 100 poise); it has the correct molecular charge to bind the dye if it is a non-covalent mixture (i.e. anionic protein and cationic dye, or cationic protein and anionic dye); it has the correct amino-acids present to form covalent cross-links (i.e. one or more tyrosines, histidines, tryptophans and/or methionines); and/or it is biocompatible (i.e. from mammalian origin for mammals, preferably from human origin for humans, from canine origin for canines, etc.; it is autologous; it is non-allergenic, and/or it is non-immunogenic).

III. Protein Analysis of Nipple Aspiration Fluid

The present invention employs methods of separating proteins from nipple aspiration fluid. Methods of separating proteins are well know to those of ordinary skill in the art and may include but are not limited to various kinds of chromatography such as: anion exchange chromatography, affinity chromatography, sequential extraction, and high performance liquid chromatography. The assay of the nipple aspiration fluid can be accomplished by gel electrophoresis using commercially available reagents. In particular embodiments the present invention employs high-resolution electrophoresis, e.g., one, two-dimensional gel electrophoresis to separated proteins from nipple aspiration fluid or blood serum. Preferably, two-dimensional gel electrophoresis is used to generate two-dimensional array of spots of proteins from nipple aspirate fluid, which may indicate markers for breast cancer. A fraction containing a marker can be isolated and further analyzed by gas phase ion spectrometry.

Two-dimensional gel electrophoresis can be performed using methods known in the art (See, e.g., Deutscher, 1999, U.S. Pat. Nos. 5,534,121 and 6,398,933). Typically, proteins in a sample are separated by, e.g., isoelectric focusing, during which proteins in a sample are separated in a pH gradient until they reach a spot where their net charge is zero (i.e., isoelectric point). This first separation step results in one-dimensional array of proteins. The proteins in one dimensional array is further separated using a technique generally distinct from that used in the first separation step. For example, in the second dimension, proteins separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of the protein. Typically, two-dimensional gel electrophoresis can separate chemically different proteins in the molecular mass range from 1000–200,000 Da within complex mixtures. Electrophoresis is the process of separating molecules on the basis of the molecule's migration through a gel in an applied electric field. In an electric field, a molecule will migrate towards the pole (cathode or anode) that carries a charge opposite to the net charge carried by the molecule. This net charge depends in part on the pH of the medium in which the molecule is migrating. One common electrophoretic procedure is to establish solutions having different pH values at each end of an electric field, with a gradient range of pH in between. At a certain pH, the isoelectric point of a molecule is obtained and the molecule carries no net charge. As the molecule crosses the pH gradient, it reaches an isoelectric point and is thereafter immobile in the electric field. Therefore, this electrophoresis procedure separates molecules according to their different isoelectric points.

Electrophoresis in a polymeric gel, such as a polyacrylamide gel or an agarose gel, adds two advantages to an electrophoretic system. First, the polymeric gel stabilizes the electrophoretic system against convective disturbances. Second, the polymeric gel provides a porous passageway through which the molecules must travel. Since larger molecules will travel more slowly through the passageways than smaller molecules, use of a polymeric gel permits the separation of molecules by both molecular size and isoelectric point.

Thus, electrophoresis in a polymeric gel can also be used to separate molecules, such as RNA and DNA molecules, which all have the same isoelectric point. These groups of molecules will migrate through an electric field across a polymeric gel on the basis of molecular size. Molecules with different isoelectric points, such as proteins, can be denatured in a solution of detergent, such as sodium dodecyl sulfate (SDS). The SDS-covered proteins will have similar isoelectric points and will migrate through the gel on the basis of molecular size. The separation of DNA molecules on the basis of their molecular size is an important step in determining the nucleotide sequence of a DNA molecule.

A polymeric gel electrophoresis system is typically set up in the following way: A gel-forming solution is allowed to polymerize between two glass plates that are held apart on two sides by spacers. These spacers determine the thickness of the gel. Typically, sample wells are formed by inserting a comb-shaped mold into the liquid between the glass plates at one end and allowing the liquid to polymerize around the mold. Alternatively, the gel may be cast with a flat top and a pointed comb inserted between the plates so that the points are slightly imbedded in the gel. Small, fluid-tight areas between the points can be filled with a sample.

The top and bottom of the polymerized gel are placed in electrical contact with two separate buffer reservoirs. Macro-molecule samples are loaded into the sample wells via a sample-loading implement, such as a pipette, which is inserted between the two glass plates and the sample is injected into the well. To prevent sample mixing, it is advantageous to inject-the sample as close to the gel as possible. It is difficult to place the tip of the pipette or loading implement close to the gel because the pipette tip is often wider than the gel.

An electric field is set up across the gel, and the molecules begin to move into the gel and separate according to their size. The size-sorted molecules can be visualized in several ways. After electrophoresis, the gels can be bathed in a nucleotide-specific or protein-specific stain which renders the groups of size-sorted molecules visible to the eye. For greater resolution, the molecules can be radioactively labeled and the gel exposed to X-ray film. The developed X-ray film will indicate the migration positions of the labeled molecules.

Both vertical and horizontal assemblies are routinely used in gel electrophoresis. In a vertical apparatus, the sample wells are formed in the same plane as the gel and are loaded vertically. A horizontal gel will generally be open on its upper surface, and the sample wells are formed normal to the plane of the gel and also loaded vertically.

Two-dimensional electrophoresis is a useful technique for separating complex mixtures of molecules, often providing a much higher resolving power than that obtainable in one-dimension separations. The technique permits component mixtures of molecules to be separated according to two different sets of properties in succession, and lends itself to a variety of different combinations of separation parameters. One combination is separation based on charge followed by separation based on molecular weight, as discussed separately above. Another is separation in a gel of one concentration followed by separation in a gel of the same material but of another concentration. Two-dimensional separations have also been used to create a stepwise change in pH, to separate first in a homogeneous gel and then in a pore gradient gel, to separate in media containing first one molecule solubilizer and then another, or in media containing a solubilizer first at one concentration and then at another concentration, to separate first in a discontinuous buffer system and then in a continuous buffer system, and to separate first by isoelectric focusing and then by homogeneous or pore gradient electrophoresis. Combinations such as these can be used to separate many kinds of molecular components, including serum or cell proteins, bacterial proteins, non-histone chromatin proteins, ribosomal proteins, mixtures of ribonucleoproteins and ribosomal proteins, and nucleic acids.

The first dimension of a two-dimensional electrophoresis system is typically performed in an elongate rod-shaped gel having a diameter in the vicinity of 1.0 mm, with migration and separation occurring along the length of the rod. Once the solutes have been grouped into individual zones along the rod, the rod is placed along one edge of a slab gel and the electric current is imposed across the rod and slab in a direction perpendicular or otherwise transverse to the axis of the rod. This causes the migration of solutes from each zone of the rod into the slab gel, and the separation of solutes within each zone.

Difficulties in two-dimensional electrophoresis arise in the handling of the rod-shaped gel after the first dimension separation has occurred and in placing the gel in contact with the slab gel to prepare for the second dimension separation. The first dimension separation is generally performed while the rod gel is still in the tube in which it was cast. Once the separation in the tube has been performed, the rod is physically removed from the tube, then placed along the exposed edge of the slab gel. The extraction of the rod from the tube and the act of placing it along the slab gel edge require delicate handling, and even with the exercise of great care, the gel is often damaged and the solute zones are distorted or disturbed. Alignment and full contact of the rod with the slab gel are important for achieving both electrical continuity and unobstructed solute migration between the gels. Furthermore, considerable time is involved in the handling and placement of the rod, and errors can result in loss of data. Gel strips can be used as alternatives to the rod, but are susceptible to similar difficulties, opportunities for error, and a lack of reproducibility.

Many of these problems are eliminated by gel packages that contain both the elongated first dimension gel and the slab-shaped second dimension gel in a common planar arrangement that permits the two separations to be done in succession without any intervening insertion or removal of either gel. One such arrangement and method of use is disclosed in U.S. Pat. No. 4,874,490.

More recently, a new pre-cast gel structure and method has been described in U.S. Pat. No. 5,773,645, which describes a combined water-swellable strip gel and a slab gel on a common support for two-dimensional electrophoresis. In this disclosure, the strip gel is isolated from the slab gel by a fluid-impermeable and electrically insulating barrier. The first dimension separation is performed by placing the liquid sample and buffer in the reservoir to cause the gel to swell and to load it with sample, and then passing an electric current through the reservoir. The barrier, which is joined to the support in an easily breakable manner, is then removed, and the strip gel is placed in contact with the slab gel for the second dimension separation.

In each case, each dimension of the two dimensional electrophoresis is performed in a physically separate gel. When the second dimension is run, the physical discontinuity of the separate gels give rise to a lack of resolution, as well as the need to carefully manipulate the gel during the course of the protocol.

Thus, it would be desirable to provide a gel system and apparatus which would allow the separation of molecules in two dimensions, relying on two separate parameters, within the same gel and not requiring a manipulation or discontinuity to establish and maintain high resolution in each dimension.

An automated system which performs the two dimensional gel electrophoresis in a single gel has been described in PCT Publication WO 96/39625 which utilizes computer controlled robotics to physically rotate the gel slab 90 degrees after the first dimension gel separation has been performed.

An electrophoresis device which eliminates the requirement to physically rotate the gel slab 90 degrees after the first dimension gel separation has been described in U.S. Pat. No. 5,562,813. The device includes an electrophoresis medium enclosed between two plates positioned in contact with a first pair and a second pair of compartments for electrophoresis liquid. Each of the compartments is provided with electrodes to make electrophoretic contact on either side and mutually transversely of each other with the electrophoresis medium, and the compartments are disposed and adapted such that the electrophoresis unit assumes a standing position in the apparatus.

In further embodiments of the present invention proteins in the two-dimensional array can be detected using any suitable methods known in the art. Staining of proteins can be accomplished with colorimetric dyes (coomassie), silver staining and fluorescent staining (Ruby Red). Similar staining for lipids can also be performed. For example, proteins in a gel can be labeled or stained (e.g., Coomassie Blue, Ruby Red, or silver staining). As is known to one of ordinary skill in the art, spots/or protein profiling patterns generated can be further analyzed for example, by gas phase ion spectrometry. Proteins can be excised from the gel and analyzed by gas phase ion spectrometry. Alternatively, the gel containing proteins can be transferred to an inert membrane by applying an electric field and the spot on the membrane that approximately corresponds to the molecular weight of a marker can be analyzed by gas phase ion spectrometry.

IV. Support Vector Machines

In further embodiments, the present invention employs a learning algorithm for evaluating and/or comparing digitalized protein profiles generated from 2-D gele electrophoresis of a sample comprising proteins. Any learning algorithm may be employed, but in specific embodiments, support vector machines (SVMs) are used. A support vector machine (SVM) is a supervised machine learning technique, which has been shown to perform well in multiple areas of biological analysis including evaluating microarray expression data (Brown et al., 2000), detecting remote protein homologies (Jaakkola et al., 1999), and recognizing translation initiation sites (Zien et al., 2000). SVMs have also been used in analyzing expression data (Mukhejee et al., 1999). SVMs have demonstrated the ability to not only correctly separate entities into appropriate classes, but also to identify instances whose established classification is not supported by the data. Expression datasets contain measurements for thousands of genes which proves problematic for many traditional methods. SVMs, though, are well suited to working with high dimensional data.

SVMs (Cristianini and Shawe-Taylor, 2000) are a relatively new type of learning algorithm, originally introduced by Vapnik and co-workers (Boser et al, 1992; Vapnik, 1998) and successively extended by a number of other researchers. Their remarkably robust performance with respect to sparse and noisy data is making them the system of choice in a number of applications from text categorization to protein function prediction.

When used for classification, they separate a given set of binary labeled training data with a hyper-plane that is maximally distant from them (known as 'the maximal margin hyper-plane'). For cases in which no linear separation is possible, they can work in combination with the technique of 'kernels', that automatically realizes a non-linear mapping to a feature space. The hyper-plane found by the SVM in feature space corresponds to a non-linear decision boundary in the input space.

Methods and systems for SVM pattern recognition are well known to those of ordinary skill in the art and as disclosed in the following patents and patent applications, all of which are incorporated herein in their entireties: U.S. Pat. Nos. 6,128,608; 6,157,921; U.S. patent application Ser. No. 09/303,386, filed May 1, 1999; U.S. patent application Ser. No. 09/303,389, filed May 1, 1999; U.S. patent application Ser. No. 09/715,832, filed Nov. 17, 2000; U.S. Pat. No. 6,427,141; U.S. Pat. No. 6,658,395: U.S. patent application Ser. No. 09/633,850, filed Aug. 7, 2000; U.S. patent application Ser. No. 09/633,615, filed Aug. 7, 2000; U.S. Patent Application Ser. No. 09/633,616, filed Aug. 7, 2000; U.S. Pat. No. 6,714,925; U.S. patent application Ser. No. 09/633,410, filed Aug. 7, 2000; U.S. Provisional Patent Application No. 60/263,696, filed Jan. 24, 2001; U.S. Provisional Patent Application No. 60/272,391, filed Mar. 1, 2001; U.S. Provisional Patent Application No. 60/275,760, filed Mar. 14, 2001; U.S. Provisional Patent Application No. 60/263,267, filed Jan. 22, 2001; U.S. Provisional Patent Application No. 60/263,381, filed Jan. 23, 2001; U.S. Provisional Patent Application No. 60/292,133, filed May 18, 2001; U.S. Provisional Patent Application No. 60/292,221, filed May 18, 2001; U.S. Provisional Patent Application No, 60/292,978, filed May 23, 2001; U.S. Provisional Patent Application No. 60/298,757, filed Jun. 15, 2001; U.S. Provisional Patent Application No. 60/298,842, filed Jun. 15, 2001; U.S. Provisional Patent Application No. 60/298,867, filed Jun. 15, 2001; and U.S. Provisional Patent Application No. 60/309,717, filed Aug. 2, 2001.

V. Diagnostics, Prognosis and Therapeutics Involved in Identifying Markers

The present invention further contemplates a method of diagnosing breast cancer comprising the steps of collecting a first sample comprising nipple aspiration fluid from a first breast cancer patient; collecting a second sample comprising nipple aspiration from a second breast of the cancer patient, wherein the first and second samples comprising fluid from the first and second breasts of the same cancer patient, wherein one breast is cancerous and the other is non-cancerous, constitutes a paired sample; separating the proteins by two-dimensional gel electrophoresis; and comparing the profiles of breast fluid proteins from the first and second sample, wherein the difference in the profiles identifies a breast cancer marker. In particular aspects, the sample is a breast fluid sample. In preferred embodiments, the invention comprises assaying for a cancer marker from the sample. In some embodiments the invention may contemplate contacting the sample with an antibody that binds immunologically to a breast cancer marker protein or peptide of the invention. In still further embodiments, the invention may further comprise subjecting proteins of the sample to ELISA. In particular aspects of the present invention, the diagnostic method further comprises the step of comparing the expression of the breast cancer marker(s) of the invention with the expression of the breast cancer marker in non-cancer samples. In more particular aspects, the comparison involves evaluating the level of expression of the breast cancer marker identified herein. In further aspects, the comparison involves evaluating the structure of the gene, protein or transcript of the breast cancer marker.

A. Prognostics

The breast cancer markers of the invention can be identified in nipple aspiration fluid samples from a breast cancer patient by comparing protein profiling of each breast in a patient with unilateral invasive breast cancer to generate a profile. As such, the breast cancer marker of the invention are useful as markers in determining whether that patient's cancer will progress and, therefore, will allow a proper determination of the need for additional therapy to be made.

The expression levels of the breast cancer markers of the invention, and other sequences, will also be useful in monitoring the effectiveness of a treatment regimen. In any event, the methods of the present invention will assist physicians in diagnosing cancer and in determining optimal treatment courses for individuals with tumors of varying malignancy.

As described herein in detail, the amount of the breast cancer markers of the invention or related cancer marker present within a biological sample, such as a tissue, blood or serum sample, may be determined by means of a molecular biological assay to determine the level of a nucleic acid that encodes such a polypeptide, or by means of an immunoassay to determine the level of the polypeptide itself.

It is envisioned that in clinical applications, nipple aspiration fluid samples will be screened for the presence of the markers of cancer identified herein. Samples may also consist of needle biopsy cores, surgical resection samples, lymph node tissue, or serum/plasma.

In certain embodiments, proteins would be collected from these samples and amplified as described above. Some embodiments may utilize kits containing pre-selected primer pairs or hybridization probes. The protein would be tested for the markers by any of the detection methods described herein or other suitable methods known in the art.

In other embodiments, nipple aspiration fluid samples containing marker proteins would be collected from a patient and subjected to an immunoassay as described herein. Immunoassays of tissue sections are also possible. Kits containing the antibodies of the invention would be useful.

Another embodiment of the present invention involves application of RT-PCR techniques to detect circulating cancer cells in blood (i.e., those that have already metastasized), using selected probes and primers. Similar techniques have been described in PCT Patent Application No. WO 94/10343, incorporated herein by reference.

The presence of the breast cancer-marker nucleic acids in nipple aspiration fluid, blood or lymph node samples is indicative of a patient with metastatic cancer, i.e., indicative of a poor prognosis.

In terms of analyzing tissue samples, irrespective of the manner in which the level of a given cancer marker is determined, the prognostic evaluation will generally require the amount of the marker in the tissue sample to be compared to the amount in normal cells, in other patients and/or amounts at an earlier stage of treatment of the same patient. Comparing the varying levels of a given marker will allow the characteristics of the particular cancer to be more precisely defined.

Thus, the levels of selected marker detected, such as the breast cancer markers of the invention, would be compared with statistically valid groups of metastatic, non-metastatic malignant, benign or normal tissue samples; and/or with earlier marker levels in the same patient. The diagnosis and prognosis of the individual patient would be determined by comparison with such groups.

Where the presence of a cancer marker correlates with cancer progression, then the clinical detection of such a marker, or an increase in the levels of such a marker, in comparison to the levels in a corresponding biological sample from a normal or even more healthy subject, is indicative of a patient with advancing cancer.

Likewise, where the absence of a cancer marker correlates with cancer progression, then the failure to clinically detect such a marker, or a decrease in the levels of such a marker, in comparison to the levels in a corresponding biological sample from a normal or even more healthy subject, would also be indicative of a patient with advancing cancer. An example is the loss, decreasing levels or mutation of a tumor suppressor.

Those of skill in the art are very familiar with differentiating between the significant expression of a biomarker, such as the breast cancer markers of the invention, which represents a positive identification, and the low level or background expression of a biomarker. Indeed, background expression levels are often used to form a "cut-off" above which increased levels are scored as significant or positive. Significant expression may be represented by high levels of nucleic acids or antigens in tissues or within body fluids, or alternatively, by a high proportion of cells from within a tissue that each give a positive signal.

If desired, the cancer screening methods of the present invention may be readily combined with other methods in order to provide an even more reliable indication of prognosis. Various markers of cancer have been proposed to be correlated with metastasis and malignancy. They are generally classified as cytological, protein or nucleic acid markers. Any one or more of such methods may thus be combined with those of this invention in order to provide a multi-marker prognostic test.

Cytological markers include such things as "nuclear roundedness" (Diamond et al., 1982) and cell ploidy. Protein markers include prostate specific antigen (PSA) and CA125. Nucleic acid markers have included amplification of Her2/neu, point mutations in the p53 or Ras genes, and changes in the sizes of triplet repeat segments of particular chromosomes.

All of the above markers exhibit certain drawbacks, associated with false positives and false negatives. A false positive result occurs when an individual without malignant cancer exhibits the presence of a "cancer marker". For example, elevated serum PSA has been associated with prostate carcinoma. However, it also occurs in some individuals with non-malignant, benign hyperplasia of the prostate.

A false negative result occurs when an individual actually has cancer, but the test fails to show the presence of a specific marker. The incidence of false negatives varies for each marker, and frequently also by tissue type. For example, Ras point mutations have been reported to range from a high of 75% in pancreatic cancer to a low of zero percent in some gynecological cancers.

Additional problems arise when a marker is present only within the transformed cell itself. Ras point mutations can only be detected within the mutant cell. This means that, in order to detect a malignant tumor, one must take a sample of the tumor itself, or its metastatic cells. Since the object of cancer detection is to identify and treat tumors before they metastasize, essentially one must first identify and sample a tumor before the presence of the cancer marker can be detected.

Finally, specific problems occur with markers that are present in normal cells but absent in cancer cells. Most tumor samples will contain mixed populations of both normal and transformed cells. If one is searching for a marker that is present in normal cells, but occurs at reduced levels in transformed cells, the "background" signal from the normal cells in the sample may mask the presence of transformed cells.

Preferred cancer markers are those that are present in malignant cancers, and either missing or else expressed at significantly lower levels in benign tumors and normal cells.

As any single marker would typically be present only in some proportion of malignant cancers, it is desirable to have a number of such markers for each cancer type.

The present invention addresses the need for cancer markers by identifying in nipple aspiration fluid a cancer marker(s) that is expressed at higher levels in malignant carcinoma than in normal tissue. In preferred embodiments, this invention provides breast cancer markers that are indicative of cancer progression and metastatic potential. This represents a significant advance. However, combination of the present techniques with one or more other diagnostic or prognostic techniques or markers is certainly contemplated. In that many cancers are multifactorial, the use of more than one method or marker is often highly desirable.

B. Therapuetics

In an embodiment of the present invention, a method of treatment for breast cancer, by the delivery of a cancer marker protein that modulates such a cancer is contemplated. Such a therapy may be administered to a patient in an effective amount to ameliorate, reduce, minimize or limit the extent of the disease or its symptoms. More rigorous definitions may apply, including elimination, eradication or cure of disease.

C. Molecular Biological Detection Kits for Breast Cancer

In some embodiments it is contemplated the aforementioned procedures of the present invention may employ the use of a kit. The materials and reagents required for detecting cancer cells in a biological sample may be assembled together in a kit. The kits of the invention will generally comprise one or more preselected primers or probes specific for the breast cancer marker of the invention. Additional primers or probes for other known breast cancer markers may also be comprised in such a kit. Preferably, the kits will comprise, in suitable container means, one or more cancer probes or primers and means for detecting such probes or primers. In certain embodiments, such as in kits for use in Northern blotting, the means for detecting the nucleic acids may be a label, such as a radiolabel, that is linked to a nucleic acid probe itself.

Preferred kits are those suitable for use in PCR. In PCR kits, two primers will preferably be provided that have sequences from, and that hybridize to, spatially distinct regions of the breast cancer marker gene. Preferred pairs of primers for amplifying nucleic acids are selected to amplify the sequences specified herein. Also included in PCR kits may be enzymes suitable for amplifying nucleic acids, including various polymerases (RT, Taq, etc.), deoxynucleotides and buffers to provide the necessary reaction mixture for amplification.

The molecular biological detection kits of the present invention, although containing at least one novel breast cancer marker nucleic acid, as disclosed herein, also may contain one or more of a variety of other cancer marker gene sequences as described above. By way of example only, one may mention other breast cancer markers such as HK2, HK3, CA, Her2-neu, as well as CEA, prostate specific antigen (PSA) sequences, probes and primers. Thus the breast cancer markers of this invention would be one of a panel of cancer markers in the kit.

In each case, the kits will preferably comprise distinct containers for each individual reagent and enzyme, as well as for each cancer probe or primer pair. Each biological agent will generally be suitable aliquoted in their respective containers.

The container means of the kits will generally include at least one vial or test tube. Flasks, bottles and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions may be provided with the kit.

In further embodiments, the invention provides immunological kits for use in detecting cancer cells, e.g., in biological samples. Such kits will generally comprise one or more antibodies that have immunospecificity for proteins or peptides encoded by the nucleic acid markers of breast cancer identified in the present invention.

As the breast cancer markers of the invention and related cancer marker proteins or peptides may be employed to detect antibodies and the anti-marker antibodies may be employed to detect cancer proteins or peptides, either or both of such components may be provided in the kit. The immunodetection kits will thus comprise, in suitable container means, the breast cancer marker or related cancer marker protein or peptide, or a first antibody that binds to such a cancer marker protein or peptide, and an immunodetection reagent.

Kits comprising antibodies, such as antibodies to the breast cancer markers of the invention, will be preferred in many cases. In more preferred embodiments, it is contemplated that the antibodies will be those that bind to the epitopes of the breast cancer markers of the invention. Monoclonal antibodies are readily prepared and will often be preferred. Where cancer marker proteins or peptides are provided, it is generally preferred that they be highly purified.

In certain embodiments, the cancer protein or peptide, or the first antibody that binds to the marker protein or peptide, such as antibodies to the breast cancer markers of the invention, may be bound to a solid support, such as a column matrix or well of a microtitre plate.

The immunodetection reagents of the kit may take any one of a variety of forms, including those detectable labels that are associated with, or linked to, the given antibody or antigen itself. Detectable labels that are associated with or attached to a secondary binding ligand are also contemplated. Exemplary secondary ligands are those secondary antibodies that have binding affinity for the first antibody or antigen.

Further suitable immunodetection reagents for use in the present kits include the two-component reagent that comprises a secondary antibody that has binding affinity for the first antibody or antigen (generally, the antibody to the breast cancer markers of the invention or the breast cancer marker peptide), along with a third antibody that has binding affinity for the second antibody, wherein the third antibody is linked to a detectable label.

As noted above in the discussion of antibody conjugates, a number of exemplary labels are known in the art and all such labels may be employed in connection with the present invention. Radiolabels, nuclear magnetic spin-resonance isotopes, fluorescent labels and enzyme tags capable of generating a colored product upon contact with an appropriate substrate are suitable examples.

The kits may contain antibody-label conjugates either in fully conjugated form, in the form of intermediates, or as separate moieties to be conjugated by the user of the kit.

The kits may further comprise a suitably aliquoted composition of the cancer protein or antigen, such as the breast cancer markers of the invention, whether labeled or unlabeled, as may be used to prepare a standard curve for a detection assay.

The kits of the invention, regardless of type, will generally comprise one or more containers into which the biological agents are placed and, preferably, suitable aliquoted. The components of the kits may be packaged either in aqueous media or in lyophilized form.

The immunodetection kits of the invention, although containing at least one novel breast cancer marker antibody or antigen as identified in the present invention, also may contain one or more of a variety of other cancer marker antibodies or antigens, if so desired. Such kits could thus provide a panel of cancer markers, as may be better used in testing a variety of patients. By way of example, such additional markers could include, other tumor markers such as Her-2 neu, BRCA1, BRCA2, PSA, SeLe$^x$, γHCG, as well as p53, cyclin D1, p16, tyrosinase, MAGE, BAGE, PAGE, MUC18, CEA, p27 and αHCG.

The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed.

The kits of the present invention will also typically include a means for containing the antibody, antigen, and any other reagent containers in close confinement for commercial sale. Such containers may include injection or blow-molded plastic containers into which the desired vials are retained.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Patients and Methods

Patients

Patients who were presented to the University of Texas M. D. Anderson Cancer Center—Nellie B. Connally Breast Center were eligible to participate in this institutional review board-approved prospective investigation if they had biopsy-proven unilateral primary invasive breast cancer and gave written consent to undergo bilateral nipple aspiration. Patients were excluded from participation if they had previously undergone subareolar surgery that might have disrupted the terminal ductal system. To determine whether NAF protein expression patterns in women with unilateral breast cancer were similar to or different from those in healthy women, individual were also eligible to participate if they were over 40 years of age and had no evidence of breast disease or cancer as evidenced by normal findings on physical examination and breast imaging.

Ductal Fluid Collection

Ductal fluid was collected by nipple aspiration using a handheld suction cup similar to nonpowered breast pumps used to express milk from lactating women. This simple device consists of a plastic cup connected to a section of polymer tubing. The tubing is attached to a standard syringe that is used to create a gentle vacuum. This device was originally used and described by Sartorius et al. (1997) and was purchased for this study from Product Health, Inc. (Menlo Park, Calif.). Before aspiration was attempted, the nipple was cleansed with a small amount of Omniprep paste (D. O. Weaver and Co., Aurora, Colo.) to remove any keratin plugs and then cleansed with an alcohol pad. A small amount of lotion was placed on the breast, and the breast was gently massaged from the chest wall toward the nipple for 1 minute. The suction cup was then placed over the nipple, and the plunger of the syringe was withdrawn to the 5 to 10 ml level until ductal fluid was visualized. The fluid droplets were collected into a 10 $\mu$l graduated micropipette (Drummond Scientific Co., Broomall, Pa.). NAF samples were obtained from both breasts, and the presence of NAF and volumes of NAF obtained were recorded for each patient and each breast.

Specimen Preparation and Two-Dimensional Polyacrylamide Gel Electrophoresis

Immediately after collection, the NAF samples were rinsed into centrifuge tubes containing sterile phosphate-buffered saline supplemented with protease inhibitors AEBSF [4-(2-aminoethyl)-benzenesulfonylfluoride HCl] (0.2 mM), leupeptin (50 pg/mL), aprotinin (2 pg/mL), and dithiothreitol (0.5 mM). The samples were then centrifuged at 1500 RPM for 10 minutes, and the supernatant was collected and suspended in a buffer containing 8M urea, 2M thiourea, 1% triton X-100, 1% DTT, and 1% ampholytes, pH 3 to 10.

Protein concentration was measured using the RC DC assay kit (Bio-Rad Laboratories, Hercules, Calif.). An aliquot of 80 pg of protein was loaded onto an 11-cm IEF strip, pH 4 to 7. Focusing was conducted on IEF cells at 250 V for 20 minutes followed by a linear increase to 8000 V for 2% hours. The focusing was terminated at 20,000 volt-hours. Strips were then equilibrated in 375 mM Tris buffer, pH 8.8, containing 6M urea, 20% glycerol, 1% DTT, and 2% sodium dodecyl sulfate. Fresh DTT was added to the buffer at a concentration of 30 mg/mL. Fifteen minutes later iodoacetamide (40 mg/mL) was added to the buffer. Fifteen minutes after the addition of iodoacetomide, strips were then loaded onto the second dimension using Criterion gradient gels (Bio-Rad) with an acrylamide gradient of 8–16%. Gels were then stained by using SyproRuby fluorescent dye.

Gel Image Analysis

Gel images were compared using PDQuest software (Bio-Rad). Analysis included spot detection and comparisons of protein patterns using internal protein standards as landmarks.

Example 2

Results

Four women, three with unilateral breast cancer and one healthy subject, took part in this study. The numbers of protein spots detected by image analysis of Sypro Ruby-stained two-dimensional gels (pH 4–7) obtained upon electrophoresis of 80 pg samples of NAF proteins are listed in Table I.

TABLE 1

Numbers of Proteins Expressed in Ductal Fluid Specimens from One Breast but Not the Other in Three Patients with Unilateral Breast Cancer and One Healthy Subject. Number of Proteins Detected only in the Indicated Breast/Total Number of Proteins Detected

|  | Breast with Cancer (or, in Healthy Subject, Left Breast) | Breast without Cancer (or, in Healthy Subject, Right Breast) |
| --- | --- | --- |
| Patient 1 | 30/1472 | 14/1456 |
| Patient 2 | 202/1428 | 54/1280 |
| Patient 3 | 70/1646 | 73/1649 |
| Healthy Subject | 3/1398 | 2/1397 |

Figure 1B:
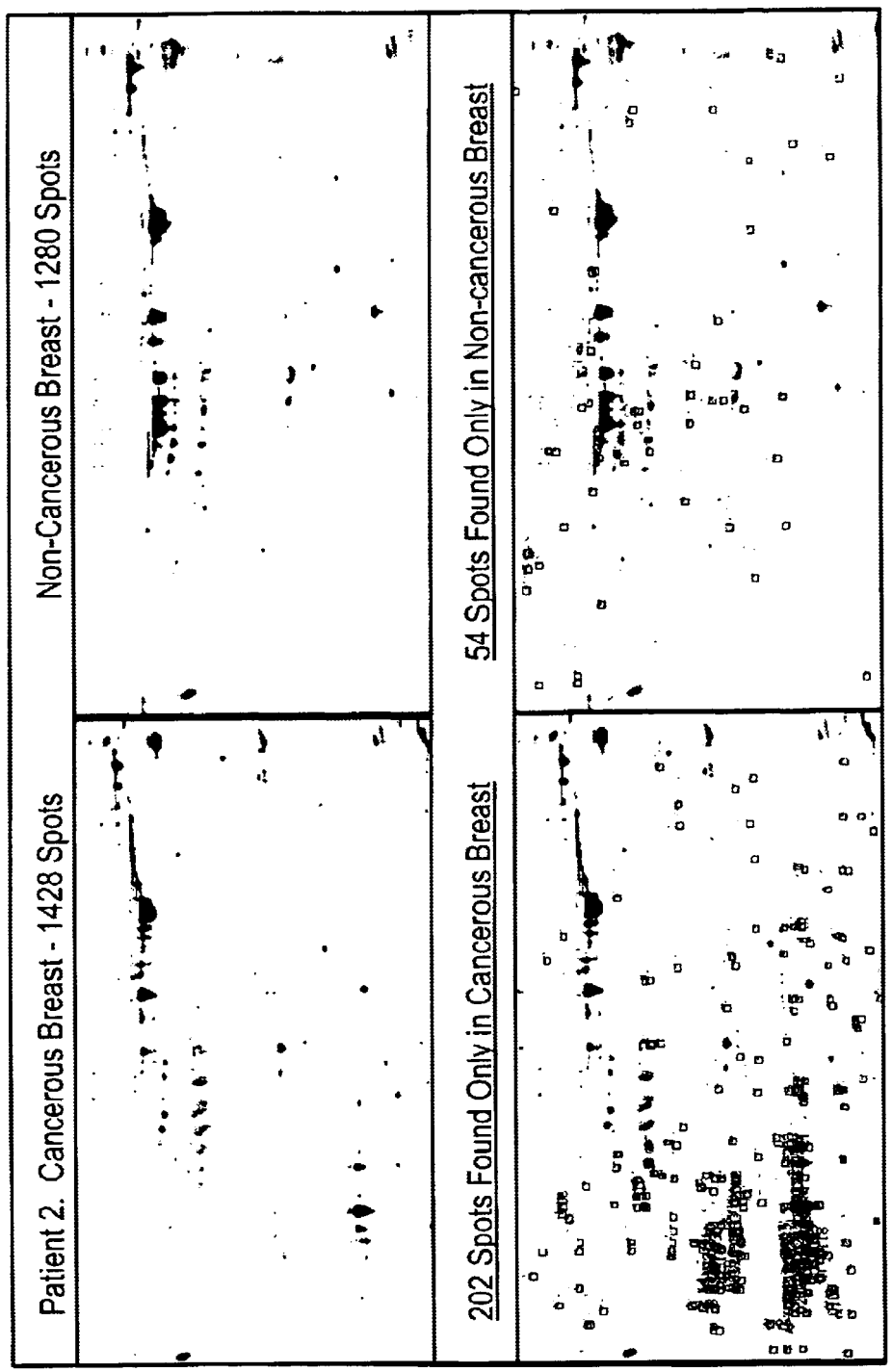
Figure 1C:
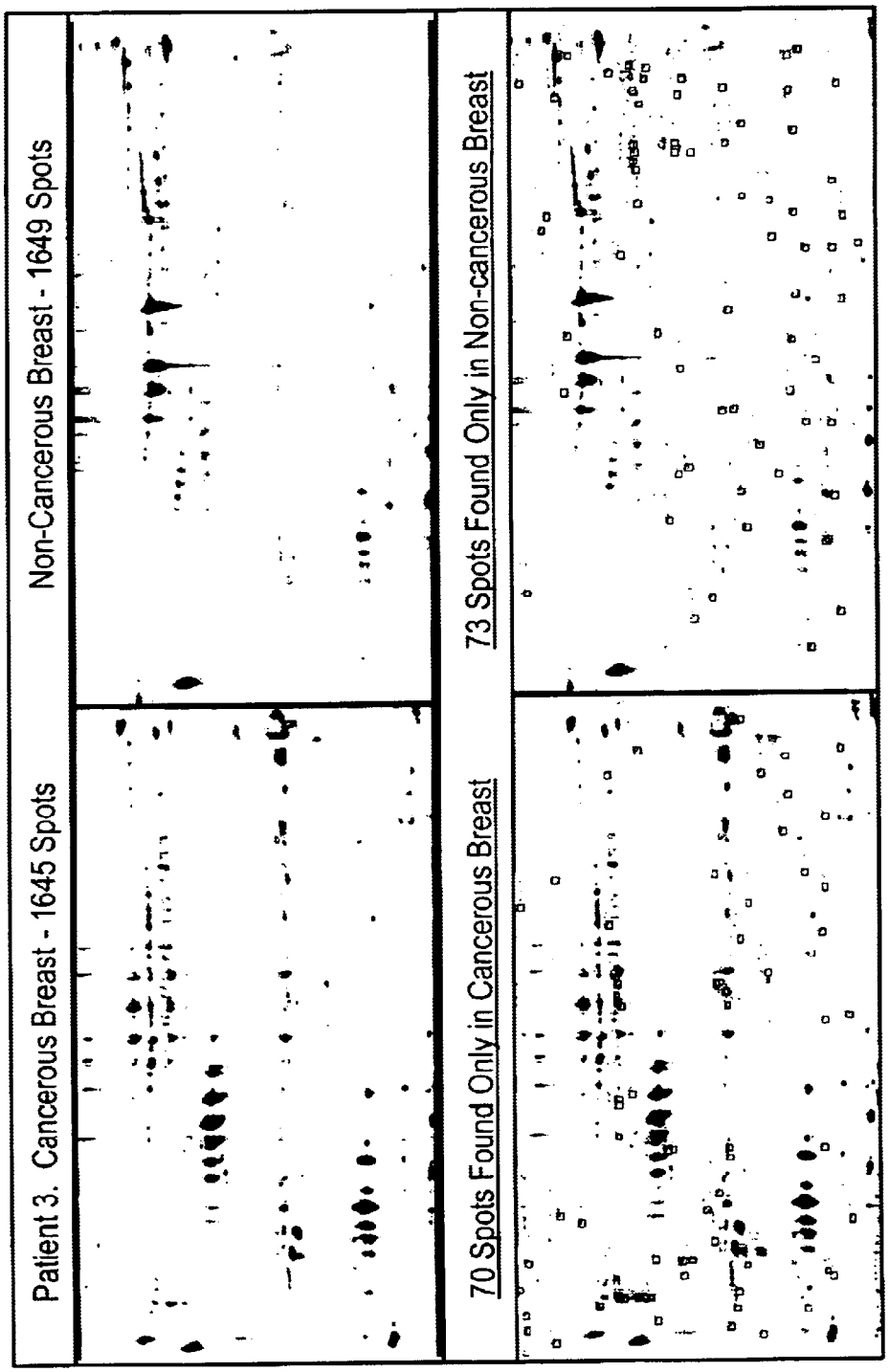
Figure 1D:
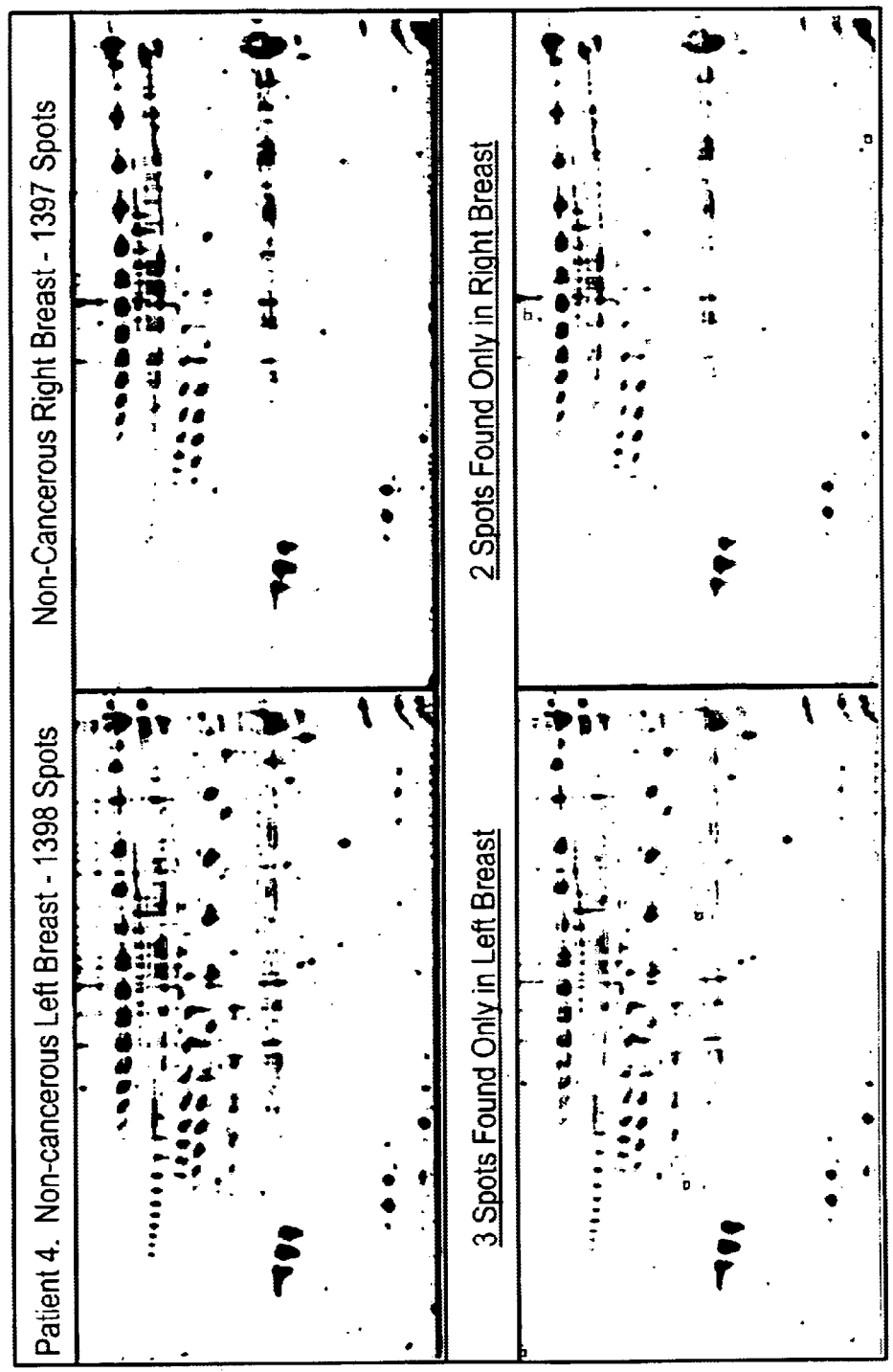

In the patients with cancer, substantial qualitative differences were identified between the protein expression patterns in the breasts with and without cancer. The number of protein spots detected in the breast with cancer and not detected in the breast without cancer in the same patient ranged from 30 to 202, and the number of protein spots detected in the breast without cancer and not detected in the breast with cancer in the same patient ranged from 14 to 73. In marked contrast, in the healthy individual, only three protein spots were detected in the left breast but not the right breast, and only two were detected in the right breast but not the left breast. The protein spot profiles on two-dimensional electrophoresis for all four study participants are shown in FIG. 1. In the patients with cancer (FIGS. 1A–1C), proteins that were detected in one breast and not in the other varied in molecular weight (vertical position), isoelectric point (horizontal position), and abundance (spot intensity), and these factors were different from patient to patient. For example, the differences were much more subtle in patient 1 (FIG. 1A) than in patient 2 (FIG. 1B). The differences found in patient 3 were of intermediate degree; the number of proteins detected only in the breast without cancer was slightly higher in this patient than in the other two. Most strikingly, the protein expression profiles for the right and left breasts of the normal individual were almost identical qualitatively (FIG. 1D).

Example 3

Discussion

The human genome contains about 35,000 protein-coding genes, and in the study described here, over 1000 separate protein species were identified in ductal fluids from the breasts of women with a unilateral breast cancer. substantial qualitative differences in protein expression between the breast with cancer and the breast without cancer was also found in each of the three patients studied. The value of nucleic acid based discovery technology, such as the use of cDNA microarrays, cannot be underestimated. However, this technology does not yield information about the post-translational modifications that are very common characteristics of carcinoma-associated proteins.

Figure 2:
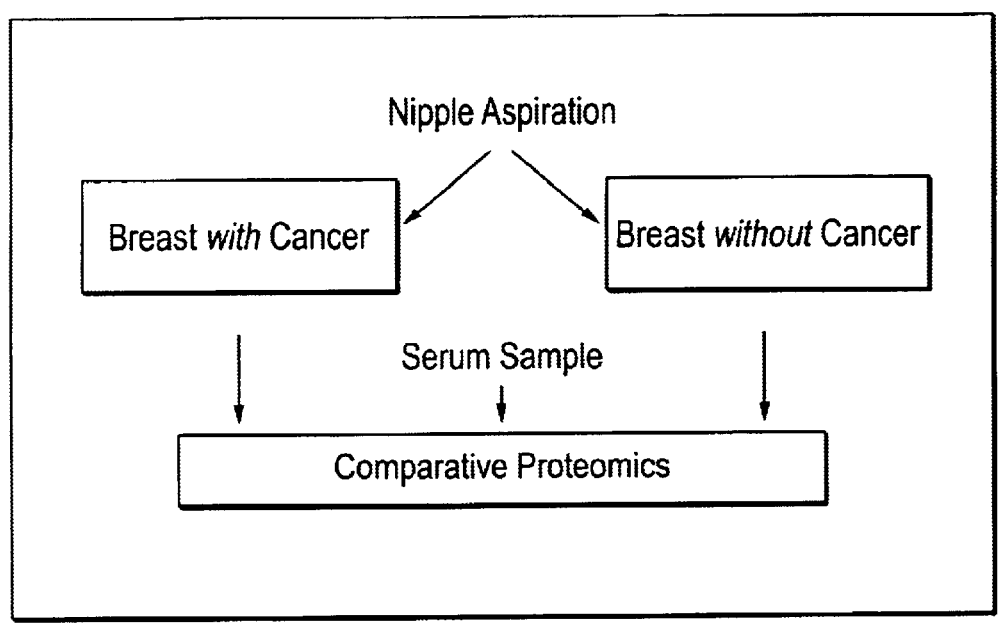
FIG. 2. The University of Texas M. D. Anderson Cancer Center Protocol for proteomic analysis of nipple aspiration fluid.

Individual profiles of proteins secreted by breast ductal cells most likely vary from one woman to another, probably as a function of an individual's specific hormonal milieu. For this reason, comparison between the breasts of an individual is an attractive approach as an internal control for these hormonal stimuli. The markedly similar protein expression profiles in the right and left breasts of the healthy volunteer in this study probably reflect a situation in which the hormonal stimulus to both breasts was more or less equal. This approach to biomarker discovery is the basis of an ongoing prospective protocol for proteomic analysis of NAF fluid at M. D. Anderson Cancer Center (FIG. 2).

Breast cancer originates from the cells lining the lobules and ducts of the breast. Nipple aspiration is a unique way of obtaining a fluid fraction that is reflective of the microenvironment where breast carcinogenesis begins. The profile of protein expression in ductal fluid from breasts with cancer is likely to reflect both cancer-specific changes as well as the host's response to the cancer. Identification of proteins that are secreted in response to carcinogenesis may also be extremely valuable in elucidation of the biology of breast cancer. Two-dimensional gel electrophoresis, the method used in this study, is currently the best method for separating complex proteins in solution. The profiles obtained by two-dimensional gel electrophoresis of proteins from NAF are an excellent source of information about the proteins secreted by the cellular constituents lining the breast ductal system, which terminates at the nipple.

The findings presented in the current study probably reflect both the largely symmetrical background hormonal effects and the effects of the cancer, seen in one breast but not the other. By using the patient as her own control, we can distinguish these two effects. It may eventually be possible to identify threshold number of qualitative differences in protein expression between an individual's breasts that signals changes associated with the presence of early-stage breast cancer. Theoretically, the occurrence of bilateral breast cancer will lead to greater than normal differences in protein expression profiles in each breast, inasmuch as the degree and stage of cancer in each breast are unlikely to be symmetrical enough to produce identical protein expression profiles in both breasts.

The analysis in the present study involved the use of highly sensitive staining techniques capable of detecting proteins in the picogram range. Large-scale analysis of protein expression in paired NAF samples from women with unilateral breast cancer and in these patients' serum has several intriguing potential uses, The most powerful information obtained from this type of analysis would be the identification of unique protein or protein expression profiles that become apparent early in breast carcinogenesis, before a tumor is detectable by physical examination or radiologic imaging. Similarly, there may be specific protein expression patterns in ductal fluids that could be used to identify women who are at high risk for the development of breast cancer.

Generation of specific information about proteins that are consistently upregulated or downregulated in ductal fluid from breasts with cancer may also be useful in our understanding of the biology of breast cancer initiation and therefore in the identification of therapeutic targets.

NAF could also be analyzed while a patient is receiving neoadjuvant chemotherapy to evaluate direct end-organ protein expression changes or other metabolites associated with response to therapy. We have been able to obtain NAF from patients who have undergone breast-conserving surgery and radiation therapy (unpublished findings). Detection of breast cancer-associated proteins in these patients could be valuable for longitudinal follow-up and early detection of in-breast recurrence. Further, comparisons in women with unilateral breast cancer between protein expression patterns in NAF fluid in the breast with cancer, the healthy contralateral breast, and the patient's serum have the exciting potential to enable identification of unique biomarkers that could be utilized to screen high-risk populations.

Lack of detection of a protein spot can be due to its absence or, possibly, to downregulation of protein expression to levels below the detection threshold of the stain. Similarly, the detection of a protein spot can be due to its induction or to upregulation to levels above the detection threshold of the stain. In fact, many of the protein differences noted in the current analysis involved proteins found in relatively low abundance, and in these cases the sensitivity of the stain used may well have played a significant role. That many of the differences found in this study involved low-abundance proteins probably reflects the fact that tumor markers and drug targets are often regulatory in nature (e.g., members of signal transduction pathways) and are often among the less abundant proteins. Differential expression of these types of proteins in low amounts (levels in the pg/mL or ng/mL range) in NAF samples from breasts with carcinoma and normal breasts has recently been shown for basic fibroblast growth factor and the HER2-neu extracellular domain.

Figure 3:
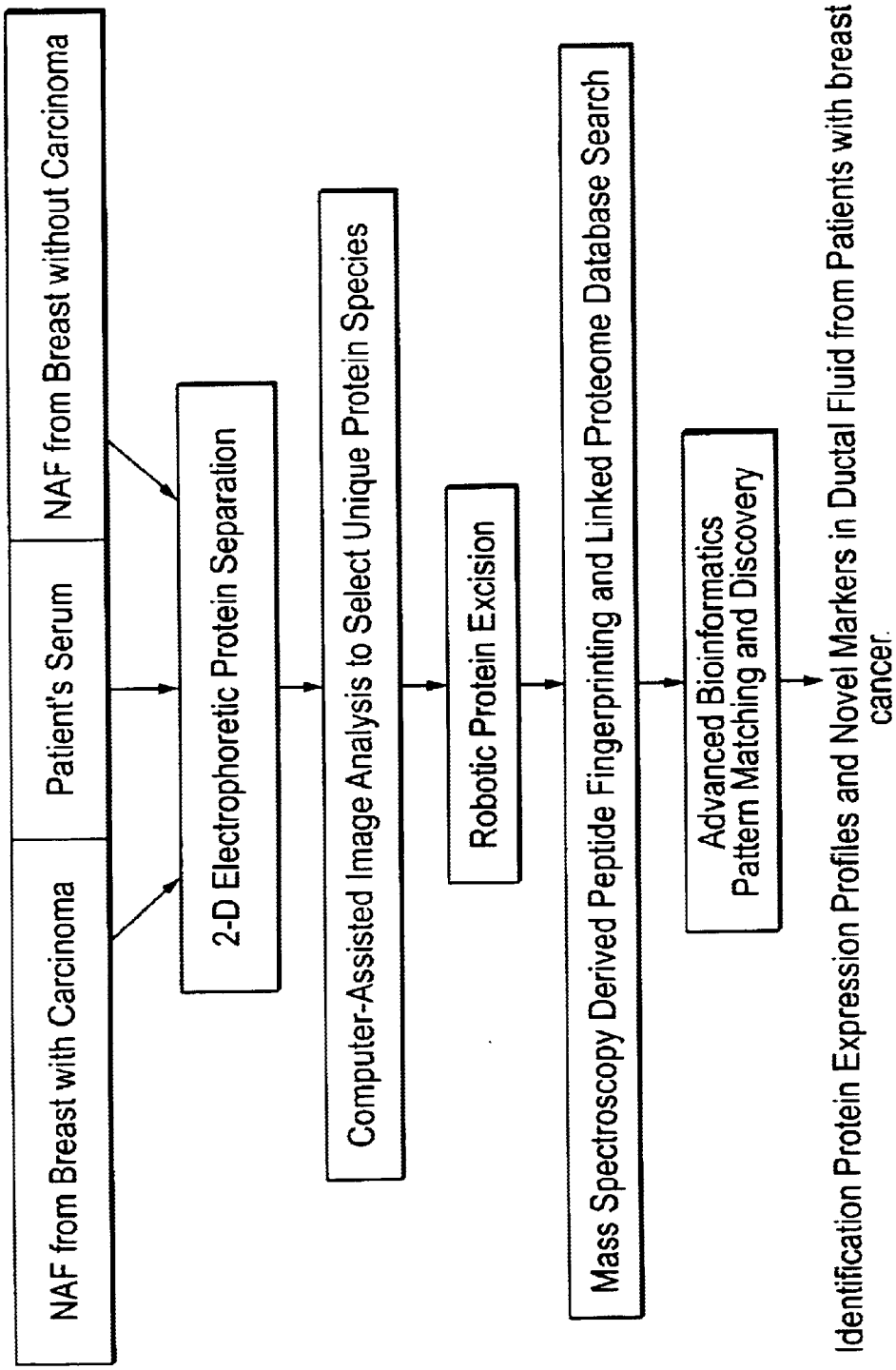
FIG. 3. Protocol for high throughput identification and characterization of unique cancer-associated proteins in ductal fluid and serum of patients with breast cancer. 2-D=two-dimensional.
Figure 4:
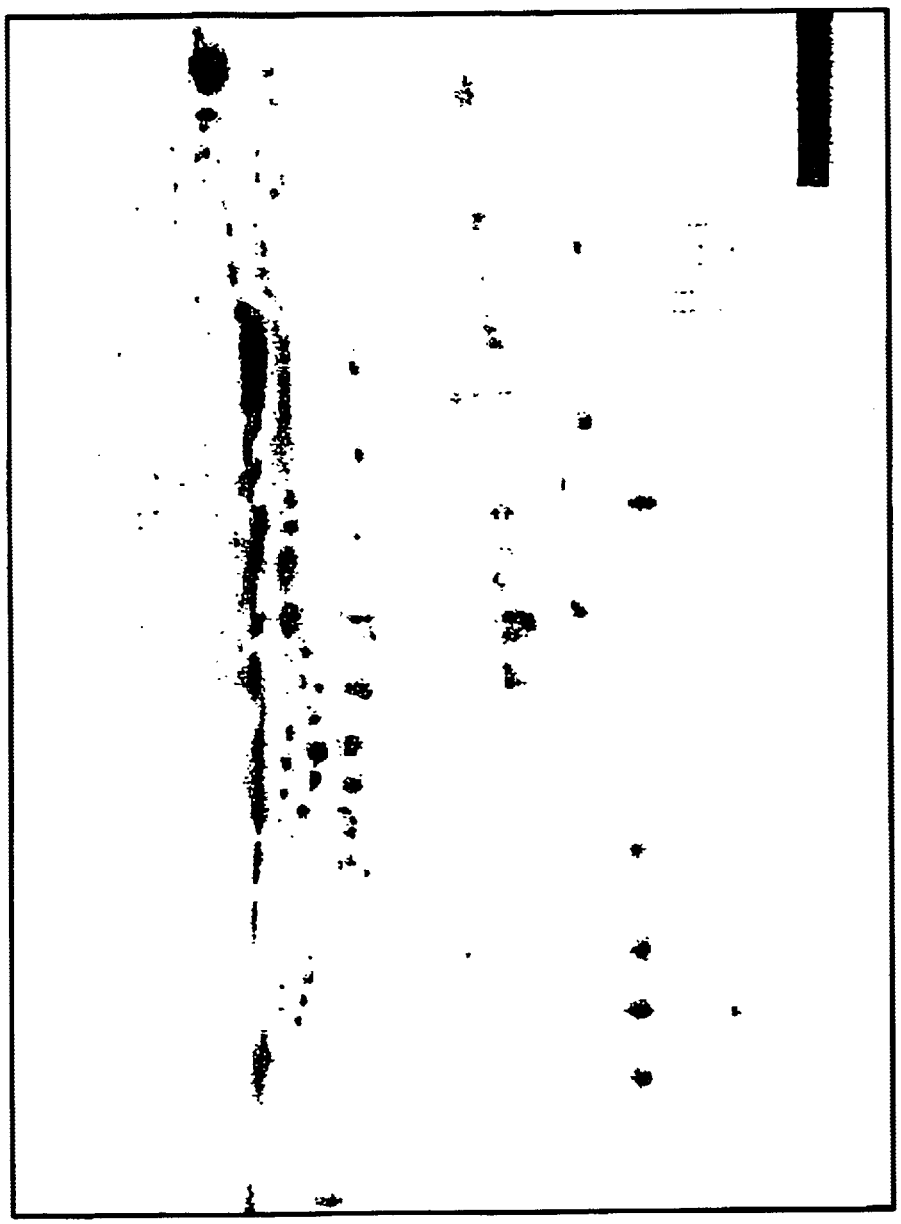
FIG. 4. Shows a 2D gel profile of nipple aspirate taken from the non-cancer breast of patient 15 with breast cancer. The proteins were visualized with Ruby Red stain.
Figure 5:
FIG. 5. Shows a 2D gel profile of nipple aspirate taken from the cancer breast from patient 15. Note that the profiles are different with gain of some proteins and loss of others between normal and cancer.
Figure 6:
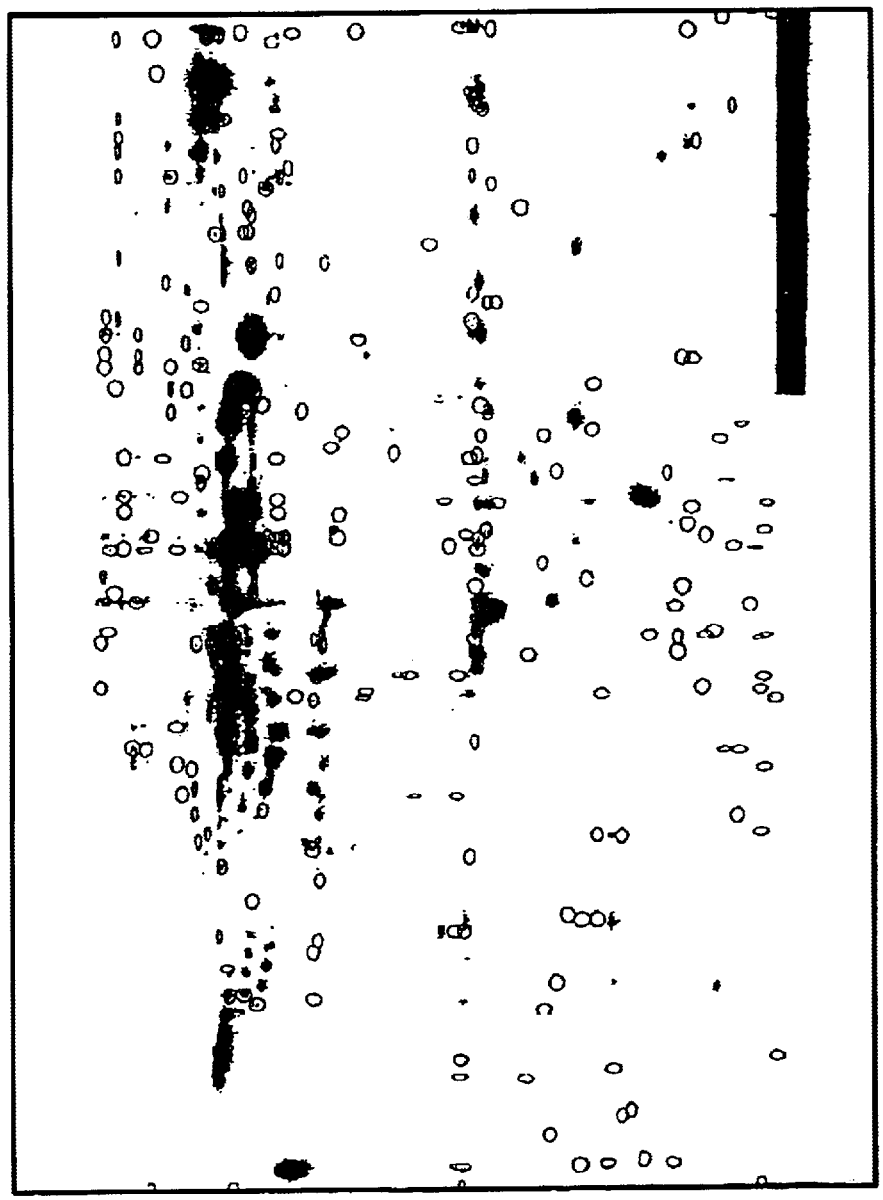
FIG. 6. Shows an overlay of FIG. 4 and FIG. 5 with the circles identifying those proteins that appear only in cancer and not in normal breast nipple aspirate. For patient 15, there are 262 spots unique to cancer.
Figure 7:
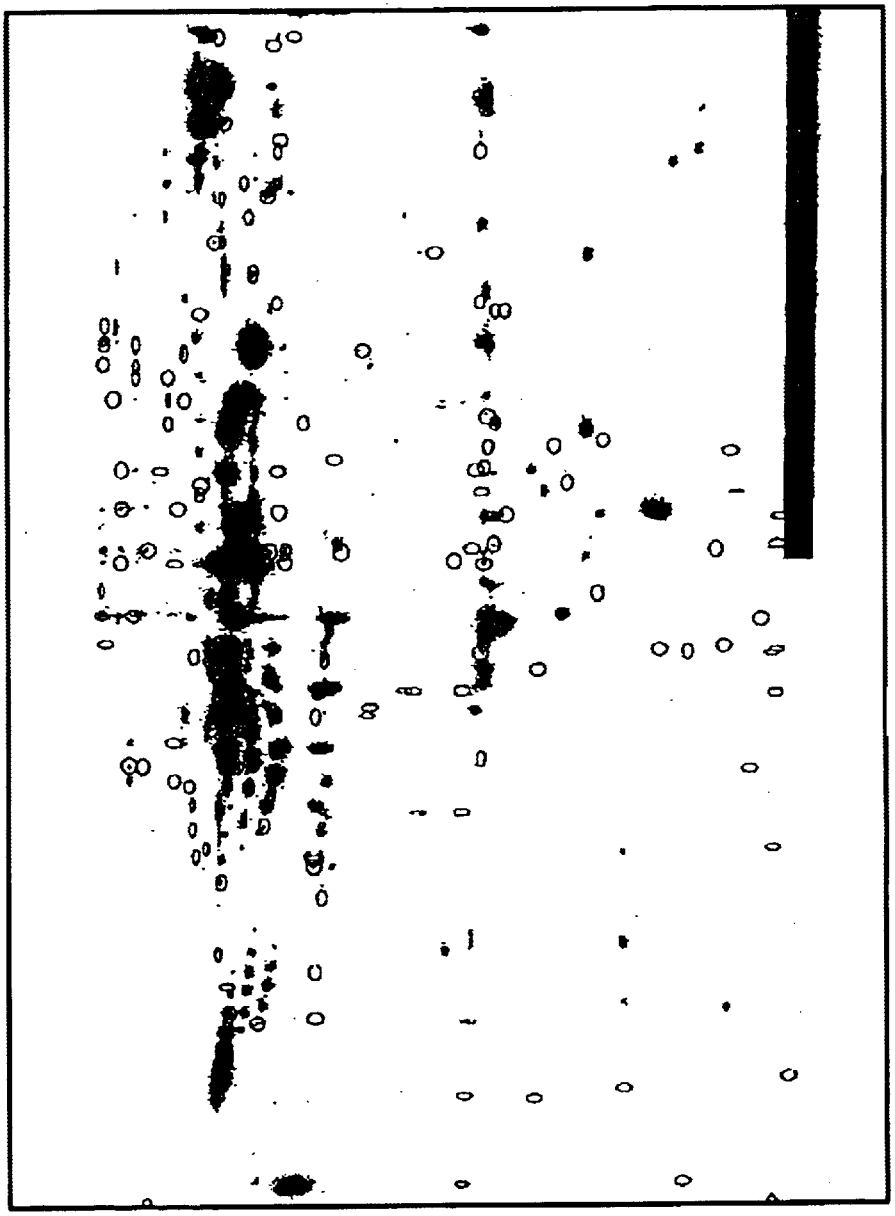
FIG. 7. Shows an overlay of FIG. 6 with the blood protein profile of patient 15 The circles indicate the 148 proteins unique to cancer that appeared to be also present in blood. These blood proteins are being characterized.

Two-dimensional electrophoresis is particularly well suited for detection of these types of changes in protein expression (FIG. 3). This technique separates proteins from complex protein solutions on the basis of protein charge and molecular weight. The introduction of digital imaging processing and computerized image analysis of the two-dimensional gels has greatly simplified the detection of unique protein species and quantification of proteins based on image intensity. By utilizing known protein species as landmarks within each gel run, computerized analysis can detect unique differences in protein expression between the breasts of an individual with unilateral breast cancer or differences in protein expression between several individuals.

Multivariate statistical analysis programs can be utilized to identify quantitative differences in protein expression among groups of samples. Proteins of interest can then be excised from the gels using robotic technology, and the exact proteins can be identified by high-throughput matrix-assisted laser desorption ionization time of flight mass spectrometry (MALDI-TOF)-based peptide mass fingerprinting and database searching or tandem mass spectrometry sequencing of individual peptides. The amount of protein in a spot needed for identification by MALDI-TOF mass peptide fingerprint analysis of in-gel tryptic digests is roughly equivalent to the limit of detection of the protein spots by the SYPRO Ruby stain utilized in this study. However, with pooling of the same spots from multiple gels, it is also possible to obtain enough material for tandem mass spectrometry peptide sequence analysis of relevant less abundant proteins that are detected. Utilizing advanced bioinformatics from paired NAF samples from women with unilateral carcinoma and a simultaneously obtained serum sample, specific protein expression patterns and novel serum markers can be correlated and identified.

Recently, investigators at the National Cancer Institute have generated proteomic spectra from serum samples in ovarian cancer patients "and from NAF samples" using a novel form of mass spectrometry called surface-enhanced laser desorption and ionization (SELDI). SELDI utilizes a precoated metal chip that binds a subset of proteins in order to categorize low-molecular-weight proteomic patterns. SELDI analysis provides a range of molecular weight patterns of a restricted number of proteins (<20 kD). In contrast, the two-dimensional gel electrophoresis approach presented in the current study encompasses a 1 O-fold broader range of proteins and enables further identification of them by conventional proteomic techniques.

Because SELDI may identify much smaller molecules and potentially relevant protein metabolites, conventional proteomic techniques and SELDI analysis of NAF may represent unique yet complementary methods of biomarker discovery.

In summary, the breast is a unique organ in that its microenvironment can be readily accessed and evaluated by aspiration of fluid from the nipple. Ductal fluids contain large amounts of protein. As the breasts are a paired organ system, significant differences may be discovered by conducting systematic comparisons of the NAF between them when cancer develops in one breast. Recent advances in image analysis, automated mass spectrometry, and bioinformatics have provided the tools necessary to utilize ductal fluids from breast cancer patients for high-throughput biomarker discovery.

All of the compositions and/or methods and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, as well as those identified in the text, are specifically incorporated herein by reference.

U.S. Patent Prov. No. 60/309,717
U.S. Patent Prov. No. 60/298,867
U.S. Patent Prov. No. 60/298,842
U.S. Patent Prov. No. 60/298,757
U.S. Patent Prov. No. 60/292,978
U.S. Patent Prov. No. 60/292,221
U.S. Patent Prov. No. 60/292,133
U.S. Patent Prov. No. 60/275,760
U.S. Patent Prov. No. 60/272,391
U.S. Patent Prov. No. 60/263,696
U.S. Patent Prov. No. 60/263,381
U.S. Patent Prov. No. 60/263,267
U.S. patent application Ser. No. 09/715,832
U.S. patent application Ser. No. 09/633,850
U.S. Pat. No. 6,714,925
U.S. patent application Ser. No. 09/633,616
U.S. patent application Ser. No. 09/633,615
U.S. patent application Ser. No. 09/633,410
U.S. Pat. No. 6,658,395
U.S. patent application Ser. No. 09/303,389
U.S. patent application Ser. No. 09/303,386
U.S. Pat. No. 5,440,013
U.S. Pat. No. 5,446,128
U.S. Pat. No. 5,475,085
U.S. Pat. No. 5,534,121
U.S. Pat. No. 5,618,914
U.S. Pat. No. 5,670,155
U.S. Pat. No. 5,672,681
U.S. Pat. No. 5,674,976
U.S. Pat. No. 5,710,245

U.S. Pat. No. 5,840,833
U.S. Pat. No. 5,859,184
U.S. Pat. No. 5,929,237
U.S. Pat. No. 6,128,608
U.S. Pat. No. 6,157,921
U.S. Pat. No. 6,398,933
U.S. Pat. No. 6,427,141
Antibodies: A Laboratory Manual, Cold Spring Harbor Laboratory, 1988.
Boser et al., In: *Proceedings of the 5th Annual ACM Workshop on Computational Learning Theory*, ACM Press, Pittsburgh, Pa., 144–152, 1992.
Brown et al., *Proc. Natl. Acad. Sci. USA*, 97:262–267, 2000.
Cristianini and Shawe-Taylor, In: *An Introduction to Support Vector Machines*, Cambridge Univ. Press, Cambridge, www.support-vector.net, 2000
Deutscher, In: *Current Protocols in Molecular Biology*, Wiley and Sons, Vol. 182; 1999
Fabian et al., *Proc. Ann. Meet. Am. Assoc. Cancer Res.*, 34:A1556, 1993.
Imayama et al, *Cancer,* 78:1229–1234, 1996.
Jaakkola et al., In: *Proceedings of the 7th International Conf. On Intelligent Systems for Molecular Biology*, AAAI Press, Menlo Park, Calif., 1999
Johannesson et al., *J. Med. Chem.*, 42(4):601–608, 1999.
Johnson et al., "Peptide Turn Mimetics" In: *Biotechnology And Pharmacy*, Pezzuto et al. (Eds), Chapman and Hall, New York, 1993.
Makita et al., *Breast Cancer Res. Treat.*, 18:179–188, 1991.
Mukhejee et al., In: *Technical Report CBCL*, Paper 182/AI Memo 1676, MIT, 1999
Okazaki et al., *Jpn. J. Clin. Oncol.*, 21:188–193, 1991.
Oz et al., *Lasers Surg. Med.*, 10(4):393–395, 1990.
Petrakis, *Breast Cancer Res Treat.*, 8:7–19, 1986.
Petrakis, *Cancer Epidem. Biomarker Prev.*, 2:3–10, 1993a.
Petrakis, *Epidem. Rev.*, 15:188–195, 1993b.
Sartorius et al., In: *Breast Carcinoma*, Logan (Ed), Wiley, NY, N.Y., 281–300, 1977.
Sartorius, *Breast Cancer Res. Treat.*, 35:255–266, 1995.
Vapnik, In: *Statistical Learning Theory*, Wiley, NY, N.Y., 1998
Vita et al., *Biopolymers,* 47(1):93–100, 1998.
Weisshoff et al., *Eur. J. Biochem.*, 259(3):776–788, 1999.
WO 97/05898
Wrensch et al., *Am. J. Epidem.*, 135:130–141, 1992.
Wrensch et al., *Breast Cancer Res. Treat.*, 15:39–51, 1990.
Wrensch et al., *Cancer Res.*, 49:2168–2174, 1989.
Zien et al., *Bioinformatics,* 16(8):799–807, 2000.

SEQUENCE LISTING [IF REQUIRED]

What is claimed is:

1. A method for identifying a marker for breast cancer comprising:
    a) collecting a first sample comprising nipple aspiration fluid from a cancerous breast of a cancer patient;
    b) collecting a second sample comprising nipple aspiration fluid from a noncancerous breast of the cancer patient, wherein the first and second samples comprising fluid from cancerous and noncancerous breasts of the same cancer patient constitutes a paired sample;
    c) separating breast fluid proteins within each of the samples by two-dimensional gel electrophoresis and forming profiles of the separated breast fluid proteins; and,
    d) comparing the profiles of breast fluid proteins from the first and second samples,
    wherein a difference in the profiles identifies a breast cancer marker.

2. The method of claim 1, further comprising staining the breast fluid proteins.

3. The method of claim 2, wherein the protein staining comprises exposing the gel to silver staining, fluorescent staining, or a colorimetric dye.

4. The method of claim 3, wherein the colorimetric dye comprises coomassie blue or ruby red.

5. The method of claim 1, further comprising generating a computer-assisted image of the profiles prior to comparing the profiles.

6. The method of claim 5, wherein a learning algorithm is employed to compare the computer-assisted images of the profiles.

7. The method of claim 6, wherein the learning algorithm is a trained support vector machine.

8. The method of claim 5, further comprising providing the computer assisted images of the profiles to a trained support vector machine.

9. The method of claim 1, further comprising collecting paired samples from additional cancer patients, and repeating steps (c–d) with the paired samples from the additional cancer patients, wherein the profiles of the paired samples identifies a pattern of breast proteins in which a breast cancer marker is identified.

10. The method of claim 9, wherein multiple breast cancer markers are identified from the pattern of breast proteins.

11. A method of detecting development or progression of breast cancer in a patient comprising:
    a) collecting a sample comprising nipple aspiration fluid from at least one breast of the patient;
    b) separating breast fluid proteins in the sample by two-dimensional gel electrophoresis; and,
    c) analyzing a breast fluid protein profile from the sample to detect a breast cancer marker identified byte method of claim 9.

12. A method of detecting development or progression of breast cancer in a patient comprising:
    a) collecting a sample comprising nipple aspiration fluid from at least one breast of the patient;
    b) assaying the sample for a breast cancer marker identified by the method of claim 9.

13. The method of claim 1, wherein nipple aspiration fluid is collected from the cancerous and noncancerous breasts of the patient using a mild suction device.

14. A method of identifying a breast cancer marker comprising:
    a) collecting a first sample comprising nipple aspiration fluid from a cancerous breast of a cancer patient;
    b) collecting a second sample comprising nipple aspiration fluid from a noncancerous breast of the cancer patient, wherein the first and second samples comprising fluid from the cancerous and noncancerous breasts of the same cancer patient constitutes a paired sample;
    c) separating breast fluid proteins within each of the samples by two-dimensional gel electrophoresis and fanning profiles of the separated breast fluid proteins; and,
    d) comparing the profiles of breast fluid proteins from the first and second samples,
    wherein a difference in the profiles identifies a breast cancer marker.

15. The method of claim 14, further comprising staining the breast fluid proteins.

16. The method of claim 15, wherein the protein staining comprises exposing the gel to silver staining, fluorescent staining, or a colorimetric dye.

17. The method of claim 16, wherein the colorimetric dye comprises coomassie blue or ruby red.

18. The method of claim 14, further comprising generating a computer-assisted image of the profiles prior to comparing the profiles.

19. The method of claim 18, wherein a learning algorithm is employed to compare the computer-assisted images of the profiles.

20. The method of claim 19, wherein the learning algorithm is a trained support vector machine.

21. The method of claim 18, further comprising providing the computer assisted images of the profiles to a trained support vector machine.

22. A method of identifying a marker for breast cancer in a patient comprising:
   a) collecting a blood serum sample from a breast cancer patient;
   b) collecting a nipple aspiration fluid sample from a cancerous breast of the breast cancer patient;
   c) separating blood serum proteins in the blood serum sample and breast fluid proteins in the nipple aspiration fluid sample by two-dimensional polyacrylamide gel electrophoresis and forming profiles of the separated proteins and,
   d) comparing a blood serum protein profile from step c) with a breast fluid protein profile from step c),
   wherein a difference in the profiles identifies a breast cancer marker.

23. The method of claim 22, further comprising stain ink the blood serum proteins and the breast fluid proteins.

24. The method of claim 23, wherein protein staining comprises exposing the gel to silver staining, fluorescent staining, or a calorimetric dye.

25. The method of claim 24, wherein the calorimetric dye comprises coomassie blue or ruby red.

26. The method of claim 22, further comprising generating a computer-assisted image of the profiles prior to comparing the profiles.

27. The method of claim 26, wherein a learning algorithm is employed to compare the computer-assisted images of the profiles.

28. The method of claim 27, wherein the learning algorithm is a trained support vector machine.

29. The method of claim 26, further comprising providing the computer assisted images of the profiles to a trained support vector machine.

* * * * *

UNITED STATES PATENT AND TRADEMARK OFFICE
CERTIFICATE OF CORRECTION

PATENT NO. : 6,855,554 B2
DATED : February 15, 2005
INVENTOR(S) : Fritsche et al.

It is certified that error appears in the above-identified patent and that said Letters Patent is hereby corrected as shown below:

Column 26,
Line 6, delete "stain ink" and replace with -- staining -- therefor.

Signed and Sealed this

Twenty-fourth Day of May, 2005

JON W. DUDAS
*Director of the United States Patent and Trademark Office*